United States Patent [19]

van Zelderen

[11] Patent Number: Plant 6,866

[45] Date of Patent: Jun. 20, 1989

[54] ALSTROEMERIA NAMED ZELPADO

[76] Inventor: Gerard J. van Zelderen, Achterweg 34-36, 1424 PR De Kwakel, Netherlands

[21] Appl. No.: 100,717

[22] Filed: Sep. 24, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinct Alstroemeria variety particularly distinguished by the generally red-purple coloration of its medium sized flowers, the petals of which have a generally red-purple coloration, the inner petals being accented by a solid white margin-to-margin coloration for the basal one-half of the petal body, the entire body of the inner petals being strongly marked with many short, longitudinally-extending and laterally-spaced pencil stripes from the petal base to its tip; the overall red-purple coloration of the flowers, with the strong white areas of the upper ones of the inner petals, providing a very striking appearance of the flower cluster. This new plant is further distinguished by its continuous year around and profuse blooming habit, its vigorous, strong and upright growth, and by the excellent lasting quality of its blooms both on the plant and as cut flowers.

1 Drawing Sheet

BACKGROUND OF THE NEW PLANT

This new Alstroemeria cultivar originated as a seedling of unknown parentage discovered among my collection of Alstroemeria varieties maintained in greenhouse at De Kwakel, Holland, for developmental purposes. This particular seedling was selected by me because of the striking, substantially overall coloration of its blooms, its profuse production of flowers the year around, and its apparent very fast and vigorous growth habit. I reproduced this seedling at De Kwakel, by root division, through several successive generations and thereby found that the novel and distinctive characteristics of flower coloration and growth habit of the new plant would remain true from generation to generation and appeared to be firmly fixed.

DESCRIPTION OF THE DRAWING

This new Alstroemeria cultivar is illustrated by the accompanying full color photographic drawing, which shows a portion of a full umbel of the inflorescence with flowers in full bloom, the color rendition being as nearly true to those specified herein as is reasonably possible to obtain by conventional photographic procedures.

DESCRIPTION OF THE NEW PLANT

The following is a detailed description of my new Alstroemeria cultivar as observed in greenhouse at De Kwakel, Holland, with the color designations being according to The R.H.S. Colour Chart of The Royal Horticultural Society of London, England.

THE PLANT

Origin: Seedling.
Parentage: Unknown.
Classification: Alstroemeria Hybrid.
Form: Erect bush.
Height: About 200 cm.
*Main stem length.*—150 to 200 cm., depending upon season.
Growth: Vigorous, strong and upright.

Rootstock: Tuberous with many buds producing flower stalks in various stages of development during the course of the year.
Branching: Each flower stalk branches at its top to form an umbel of flower bearing stems.
Foliage:
*Quantity.*—Medium.
*Leaf size.*—Depending on season.
*Leaf shape.*—Elliptic with entire margins.
*Texture.*—Leathery.
*Color.*—Middle green; sometimes showing a little anthocyanine.

THE BUD

Form: Pear shaped.
Size: Medium.
*Diameter.*—About 2 cm.
*Length.*—About 4 cm.
Opening rate: Normal.
Calyx: Long pointed and rarely splitting.

THE FLOWER

Blooming habit: Continuous the year around.
Flower size: Medium.
*Diameter.*—About 6 to 6.5 cm.
*Depth.*—About 4.5 cm.
Borne: Singly on an umbel stem.
Shape: When mature, it is funnel-like with the petal tips curling outward.
Petalage:
*Number of petals.*—Six.
*Arrangement.*—Two concentric groups each of three petals.
*Form.*—Ovate with obcordate apex.
*Texture.*—Leathery.
*Aspect.*—Velvety.
*Color.*—Outer petals: Body — 71 A-B overall with a few longitudinal pencil stripes at the tip margins. Reverse side — 71 A-B. Inside petals: The upper petals have a solid white coloration (155 D) at the inner half of the petal body with 71 A-B over the outer half of the upper petals and over the entire body of the lower one of the inside petals. Reverse side — Same as the upper side.

Peduncle:

*Length.*—About 2 cm.

*Color.*—Middle green.

Persistence: The flower petals hang on and dry.

Lasting quality:

*On the plant.*—About 21 days.

*As a cut flower.*—About 14 days.

THE REPRODUCTIVE ORGANS

Stamens:

*Number.*—Six.

*Arrangement.*—One opposite each petal.

*Anthers.*—Size: About 0.8 cm. Color: Grey-Brown.

*Filaments.*—Length: About 5 cm. Color: Pink.

*Pollen.*—Color: Blue-Grey.

Pistils:

*Number:* One.

*Style.*—Length: Varies with age. Color: Dark Pink-Purple.

*Stigma.*—Color: Purple.

I claim:

1. The new and distinct variety of Alstroemeria plant and parts thereof, substantially as herein shown and described, characterized by the distinctive red-purple coloration of its medium sized flowers, the upper ones of the inner petals having a white middle portion of its body, and by its continuous year around blooming habit.

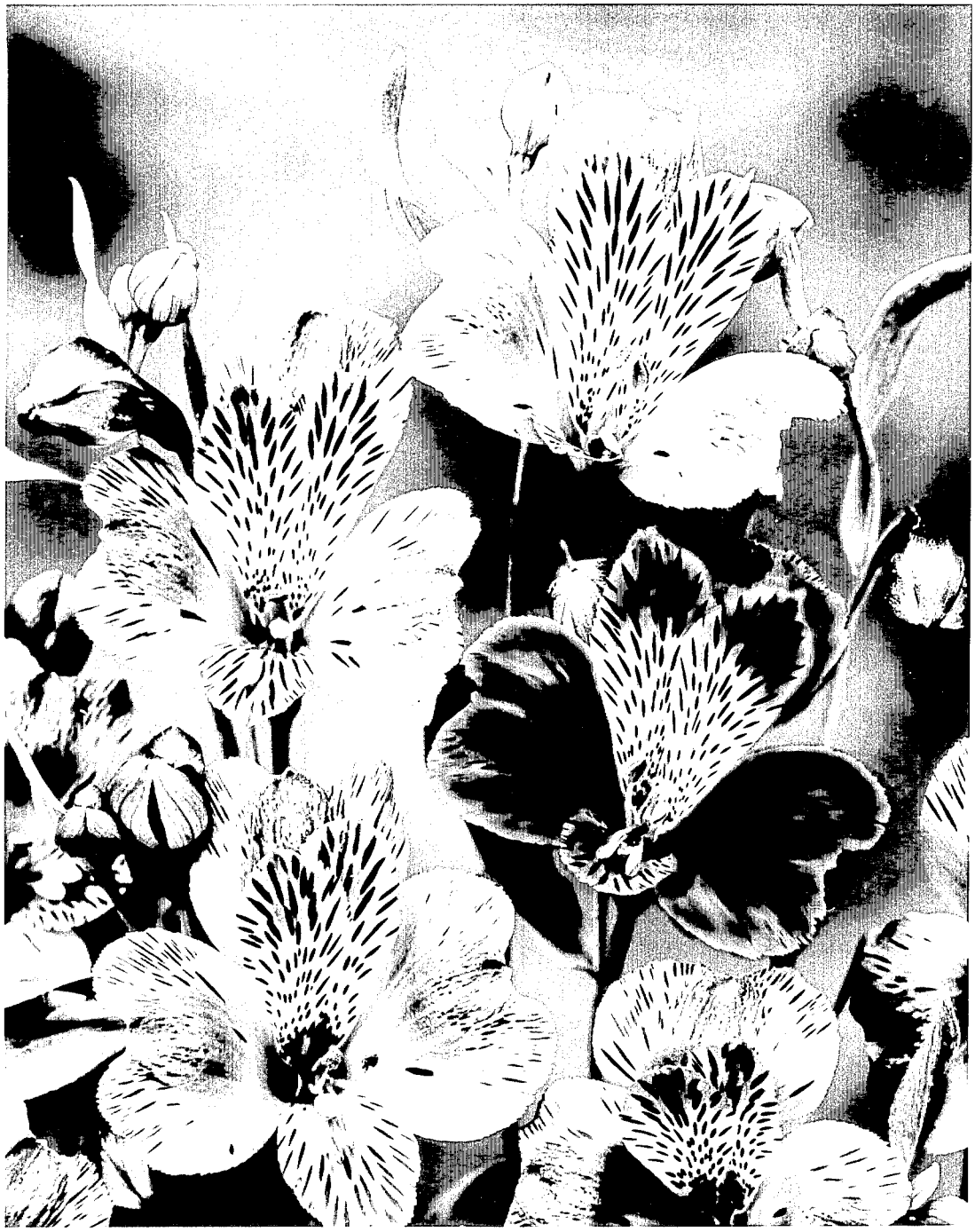

* * * * *